United States Patent
Farng et al.

(10) Patent No.: US 8,653,055 B2
(45) Date of Patent: Feb. 18, 2014

(54) CORTICOSTEROID HAVING LOW SYSTEMIC ABSORPTION

(75) Inventors: Richard K. Farng, East Brunswick, NJ (US); Chung-Tsin Chiu, Miami, FL (US); Ba Cuong Tu, Miami, FL (US); Kenneth W. Kwochka, St. Joseph, MO (US)

(73) Assignee: Teva Animal Health, Inc., Saint Joseph, MO (US)

( * ) Notice: Subject to any disclaimer, the term of this patent is extended or adjusted under 35 U.S.C. 154(b) by 1199 days.

(21) Appl. No.: 11/662,538

(22) PCT Filed: Sep. 15, 2005

(86) PCT No.: PCT/US2005/032641
§ 371 (c)(1),
(2), (4) Date: Jul. 23, 2007

(87) PCT Pub. No.: WO2006/031848
PCT Pub. Date: Mar. 23, 2006

(65) Prior Publication Data
US 2007/0299044 A1 Dec. 27, 2007

Related U.S. Application Data

(60) Provisional application No. 60/610,139, filed on Sep. 15, 2004.

(51) Int. Cl.
*A61K 31/56* (2006.01)
*A61P 29/00* (2006.01)

(52) U.S. Cl.
USPC .......................................... 514/178; 514/171

(58) Field of Classification Search
None
See application file for complete search history.

(56) References Cited

U.S. PATENT DOCUMENTS

| | | | | |
|---|---|---|---|---|
| 4,048,310 | A * | 9/1977 | Chen et al. | 514/174 |
| 4,525,346 | A | 6/1985 | Stark | |
| 4,867,970 | A * | 9/1989 | Newsham et al. | 514/31 |
| 5,380,303 | A * | 1/1995 | Holly et al. | 604/290 |
| 5,476,660 | A * | 12/1995 | Somasundaran et al. | 424/401 |
| 5,534,246 | A * | 7/1996 | Herb et al. | 424/66 |
| 5,540,930 | A * | 7/1996 | Guy et al. | 424/427 |
| 5,700,814 | A * | 12/1997 | François et al. | 514/321 |
| 6,114,377 | A * | 9/2000 | Schnittger et al. | 514/461 |
| 6,440,964 | B1 * | 8/2002 | Cagle et al. | 514/230.5 |

FOREIGN PATENT DOCUMENTS

| WO | WO-01/70270 A2 | 9/2001 |
|---|---|---|
| WO | WO-03/086348 A1 | 10/2003 |
| WO | WO-2004/043470 A1 | 5/2004 |
| WO | WO-2004/058273 A1 | 7/2004 |

OTHER PUBLICATIONS

Kurucz I, Toth S, Nemeth KT, Csillik-Perczel V, Pataki A, Salamon C, Nagy Z, Szekely JI, Horvath K, Bodor N. Potency and Specificity of the Parmacological Action of a New, Antiasthmatic, Topically Administered Soft Steroid, Etiprednol Dicloacetate (BNP-166). The Journal of Pharmacology and Experimental Therapeutics, 2003, vol. 307 No. 1, pp. 83-92.*

* cited by examiner

*Primary Examiner* — Robert A Wax
*Assistant Examiner* — Danah Al-Awadi
(74) *Attorney, Agent, or Firm* — RatnerPrestia

(57) ABSTRACT

The invention provides novel compositions of water-insoluble corticosteroid drug in combination with antimicrobial agents and very low concentrations of polymers and surfactants for topical, otic and ophthalmic treatment. The invention provides stable aqueous suspension where the ingredients remain in such a state so as to allow for immediate re-suspension, when desired, even after extended periods of settling. The invention provides also a method for treating inflammation with low systemic absorption and side-effects of the corticosteroid.

54 Claims, No Drawings

CORTICOSTEROID HAVING LOW SYSTEMIC ABSORPTION

CROSS REFERENCE TO RELATED APPLICATIONS

The present application is a national phase entry under 35 U.S.C. §371 of International Application No. PCT/US2005/032641, filed Sep. 15, 2005, published in English, which claims the benefit of U.S. Provisional Patent Application No. 60/610,139, filed Sep. 15, 2004. The disclosures of all of said applications are incorporated by reference herein.

BACKGROUND OF THE INVENTION

Typically topical, otic, or ophthalmic products containing water insoluble steroid(s) alone or in combination with antimicrobial agent(s) are very greasy because of mineral oil or petrolatum present in the suspension. Such products are very hard to instill and spread into the ear canal or skin folds, especially on haired areas. In the case of otic application, the "oily residue" stays in the ear canal after application for prolonged periods of time, which is not desirable.

There are some aqueous suspensions (for example, Lotemax Suspension, for ophthalmic use) or oil-in-water lotion products for topical use. However, many of these products still leave non-drug residues because of high concentrations of suspending agents (0.2% w/w for example), surfactants (2-5% w/w) and/or oily components (2-10% w/w) which may cause harmful effects. The ideal topical, otic, or ophthalmic formulation should be low in residues, isotonic, aqueous based, and physically and chemically stable.

In U.S. Pat. No. 5,540,930, the non-ionic polymer concentration in its steroid composition is about 0.2-2% w/w and the claimed molar concentration range for the steroid:non-ionic-polymer:surfactant is between about 1:20:1 and about 1:0.01:0.5. U.S. Pat. No. 5,540,930 indicates that the polymer used in the formulation has to be non-ionic.

A reduction in amount of polymer and surfactant used in a steroid composition should be beneficial to the biological membrane. Thus, there exists a need for aqueous suspensions of water insoluble corticosteroids, which are free of problems of prior art formulations which can be easily applied.

SUMMARY OF THE INVENTION

The present invention provides formulations having very low concentrations of non-ionic polymers and very low concentrations of surfactants. The present invention also provides formulations having ionic polymers and very low concentrations of surfactants. It is surprisingly found that at the low concentrations of non-ionic polymers (e.g., 0.005% to 0.2% w/w), the re-suspension of the drug substance is better than the formulation comprising conventional concentrations (i.e., 0.2-2% w/w) of non-ionic polymers. The following table shows molar ratios of steroid, polymers, and surfactant that can be used in this invention. These molar ratios of non-ionic polymer and surfactant range from about 1.7 to more than 1300 fold below the limits of U.S. Pat. No. 5,540,930,

| | MW | % w/w | mM | Molar ratio | U.S. Pat. No. 5,540,930 Molar Ratio Lower limit |
|---|---|---|---|---|---|
| Etiprednol Dicloacetate | 485.41 | 0.2 | 4.120228 | 1 | 1 |
| Methocel ® F4M | 86,000 | 0.005-0.2 | 0.005814-0.0232558 | 0.000141-0.0056443 | 0.01 |
| Merquat ® 550 (9% solid) | 1,600,000 | 0.005-2 | 0.000313-0.0125 | 0.0000076-0.003034 | Doesn't have non-ionic polymers. |
| Tyloxapol | 5,000 | 0.005-0.3 | 0.01-0.2 | 0.0024271-0.0485410 | 0.5 |
| Loteprednol etabonate | 466.96 | 0.2 | 4.2830221 | 1 | 1 |
| Methocel ® F4M | 86,000 | 0.005-0.2 | 0.005814-0.0232558 | 0.000141-0.0056443 | 0.01 |
| Merquat ® 550 (9% solid) | 1,600,000 | 0.005-2 | 0.000313-0.0125 | 0.0000076-0.003034 | Doesn't have non-ionic polymers. |
| Tyloxapol | 5,000 | 0.005-0.3 | 0.01-0.2 | 0.0024271-0.0485410 | 0.5 |

In addition to the unexpected improvements in physical properties, the use of low concentrations of surfactant and non-ionic polymer also surprisingly improves the pharmacological profile when compared to the formulation of drug suspended in mineral oil or without polymer. This second unexpected result is the reduction in systemic absorption of steroid, which is highly desirable given the side effects of steroidal drugs. Furthermore, contrary to U.S. Pat. No. 5,540,930, which is limited to non-ionic polymer only, however, we have also discovered that ionic polymers (e.g., MERQUAT® 550 polyquaternium 7 and/or Xanthan gum) also work well in the present steroidal formulations.

Thus, surprisingly, we have found that by reducing the concentration of surfactant (e.g., Tyloxapol) from the prior art teaching of 0.3-2% w/w to 0.005-0.3% w/w and by either adding an ionic polymer or a low concentration, 0.005-0.2% w/w, of non-ionic polymer, the systemic absorption and as a consequence, the systemic (side) effect of anti-inflammatory corticosteroids, could be reduced by approximately 60%.

DETAILED DESCRIPTION OF THE INVENTION

A soft steroid antimicrobial combination topical and/or otic formulation has broad application for inflammatory conditions complicated by secondary bacterial and/or fungal infections. In fact, most ear and skin infections in companion animals are precipitated by an inflammatory process.

Examples of cutaneous and otic inflammatory diseases include but are not limited to:

Parasites such as *Otodectes cynotis, Demodex* spp., *Sarcoptes scabiei, Notoedres cati, Cheyletiella* spp., *Ctenocephalides felis*

Foreign bodies such as plant awns

Hypersensitivity and allergic diseases such as atopic dermatitis and otitis, food related dermatitis and otitis, contact allergic and irritant cutaneous and otic reactions, feline eosinophilic dermatitis Autoimmune diseases such as pemphigus foliaceus, pemphigus erythematosus, pemphigus vulgaris, pemphigus vegitans, discoid lupus erythematosus, cutaneous vasculitis, bullous pemphigoid, and mucous membrane pemphigoid Bacterial and fungal infections may present secondary to the above inflammatory diseases or as primary infections. Common canine and feline cutaneous and/or otic pathogens include but are not limited to:

*Staphylococcus intermedius*
*Staphylococcus aureus*
*Staphylococcus schleiferi*
*Pseudomonas aeruginosa*
*Streptococcus* spp.
*Proteus mirabilis*
*Escherichia coli*
*Corynebacterium* spp.
*Enterococcus* spp.
*Malassezia pachydermatis*
*Candida* spp.

Systemic side effects are a limiting factor in the long-term use of anti-inflammatory corticosteroids. These side effects are well documented and include suppression of the adreno-pituitary axis resulting in Cushing-syndrome, immunosuppression by a reduction in cell-mediated immunity and decreased antibody production, thus, increasing the risk of infections, retention of sodium and water and hence edema, urinary potassium increase, which leads to hypokalemia and metabolic alkalosis, hyperglycemia, delay in wound healing, altered calcium metabolism with prolonged treatment, resulting in osteoporosis and bone fractures, reduction in GI motility, thinning of the gastric mucosa, and reduced mucus production, thus resulting in gastrointestinal ulceration.

Therefore, a significant reduction in systemic absorption of steroid from formulation, which results in a safer long-term use of corticosteroids is highly desirable.

Some of the materials and their sources that can be used in the current inventions are listed below. The first table lists examples of water insoluble corticosteroids and anti-microbial agents that can be combined with the steroids. More than one steroid or more than one anti-microbial can be used in the present invention.

| Drug substance | Manufacturer | Address |
| --- | --- | --- |
| Hydrocortisone Acetate micronized | Shandong Xinhua | China |
| Hydrocortisone Acetate micronized | Roussel Uclaf | Paris, France |
| Betamethasone dipropionate micronized | Sicor | Via Terrazzano, Italy |
| Betamethasone dipropionate Micronized | Pfizer | Kalamazoo, MI |
| Betamethasone Valerate, Micronized | Pfizer | Kalamazoo, MI |
| Triamcinolone acetonide, Micronized | Pfizer | Kalamazoo, MI |
| Clotrimazole micronized | Erregierre, S.p.A. | Sovere, Italy |
| Polymyxin B sulfate | Alphrama APS | Copenhagen, Denmark |

| Generic name | Trade Name | Manufacturer | Address |
| --- | --- | --- | --- |
| Hydroxypropylcellulose | Klucel GF Pharm | Hercules | Wilmington DE |
| HydroxyETHYLcellulose | Natrosol 250HHX | Hercules | Wilmington DE |
| HydroxyETHYLcellulose | Natrosol 250H | Hercules | Wilmington DE |
| Hydroxypropylmethylcellulose | Methocel ® F4M Prem | Dow Chem | Midland Michigan |
| Hydroxypropylmethylcellulose | Methocel ® K4M Prem | Dow Chem | Midland Michigan |
| Polyvinyl alcohol | Celvol V540 | Celanese | Dallas, Tx |
| Polyethylene glycol | Polyox WSR N60K NF | Dow Chem | Midland Michigan |
| Xanthan gum | Kaltrol CGF | Kelco Biopolymers | Chicago, IL |
| Polyquaternium 7 series | Merquat ® 550 (9% solid) | Nalco | Naperville, IL |
| Tyloxapol | Tyloxapol, USP | Ruger Chemical Co. | Irvington, NJ |

Additional surfactants include, but are not limited to, polysorbate 80, TWEEN 80 surfactant (ICI America Inc., Wilmington, Del.), PLURONIC F-68 surfactant (from BASF, Ludwigshafen, Germany) and poloxamer surfactants. Additional non-ionic polymers include, but are not limited to dextrans and other hydroxypropylmethylcelluloses, hydroxyethylcelluloses, hydroxypropylcelluloses, polyvinyl alcohols, and polyethylene glycols not listed above. Additional ionic polymers include, but are not limited to other xanthan gums and other highly charged cationic homo- or co-polymers (e.g., other copolymer of diallyl dimethyl ammonium chloride and acrylamide) not listed above.

The amount of surfactant present can range from 0.005, 0.006, 0.007, 0.008, 0.009, 0.01, 0.02, 0.03, 0.04, 0.05, 0.06, 0.07, 0.08, 0.09, 0.10, 0.20, to 0.3% w/w, with other ranges and examples including (a) 0.005, 0.006, 0.007, 0.008, 0.009, 0.01, 0.02, 0.03, 0.04, 0.05, 0.06, 0.07, 0.08, 0.09, 0.10, 0.20, to <0.3% w/w, (b) 0.005, 0.006, 0.007, 0.008, 0.009, 0.01, 0.02, 0.03, 0.04, to 0.05% w/w, and (c) 0.01% w/w. When no ionic polymer is present in the formulation, then the amount of surfactant present is preferably <0.3% w/w. The amount of non-ionic polymer present can range from 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, to 0.20% w/w with other ranges and examples including (a) 0.005, 0.006, 0.007, 0.008, 0.009, 0.01, 0.02, 0.03, 0.04, 0.05, 0.06, 0.07, 0.08, 0.09, 0.10, 0.11, 0.12, 0.13, 0.14, 0.15, 0.16, 0.17, 0.18, 0.19, to <0.20% w/w, (b) 0.005, 0.006, 0.007, 0.008, 0.009, 0.01, 0.02, 0.03, 0.04, to 0.05% w/w, and (c) 0.01% w/w. When no ionic polymer is present in the formulation, then the amount of non-ionic polymer present is preferably <0.2% w/w. The amount of ionic polymer is not specifically limited, but can range from 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 0.20, 0.30, 0.40, 0.50, 0.60, 0.70, 0.80, 0.90, 1.0, 1.1, 1.2, 1.3, 1.4, 1.5, 1.6, 1.7, 1.8, 1.9, to 2.0% w/w with other ranges and examples including (a) 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 0.20, 0.30, 0.40, 0.50, 0.60, 0.70, 0.80, 0.90, to 1.0% w/w, (b) 0.01, 0.02, 0.03, 0.04, 0.05, 0.06, 0.07, 0.08, 0.09, 0.10, 0.20, 0.30, 0.40, to 0.50, % w/w, (c) 0.01, 0.02, 0.03, 0.04, 0.05, 0.06, 0.07, 0.08, 0.09, 0.10, 0.11, to 0.12% w/w, (d) 0.12% w/w and (e) 0.01% w/w. Both a non-ionic and ionic polymer can be present in the present invention.

factant pairs include, but are not limited to BRIJ® 72 etherified polyethylene glycol/BRIJ® 721, etherified polyethylene glycol BRIJ® 78 etherified polyethylene glycol/ARLACEL™ 60, sorbitan stearate surfactant, BRIJ® 72 etherified polyethylene glycol/BRIJ® 78, etherified polyethylene glycol, and BRIJ® 52 etherified polyethylene glycol/BRIJ® 58 etherified polyethylene glycol (BRIJ® surfactants are etherified polyethylene glycols, which are available from Uniqema) (ARLACEL™ 60 is a sorbitan stearate surfactant available from Uniqema). The amount of second surfactant present can be from about 0.1 to 2% w/w. This amount includes the total amount of second surfactant, if the second surfactant is a pair (or more). The molar ratio of second surfactant to corticosteroid can be about 1:1.2 to 1:10 and 1:7 to 1:9. This ratio includes the total amount of second surfactant, if the second surfactant is a pair (or more).

EXAMPLES

Formulations in this invention include the following.

| | ED-Poly-B-Clo Otic suspension | | | | | | |
|---|---|---|---|---|---|---|---|
| Ingredients | 1578-57A % w/w | 1578-64 % w/w | 1578-89T % w/w | 1578-90B % w/w | 1578-90D % w/w | 1578-90E % w/w | 1578-90F % w/w |
| Etiprednol dicloacetate | 0.2 | 0.2 | 0.2 | 0.2 | 0.2 | 0.2 | 0.2 |
| Polymyxin B sulfate 10,000 U/g | 0.125 | 0.125 | 0.125 | 0.125 | 0.125 | 0.125 | 0.125 |
| Clotrimazole Micronized | 1 | 1 | 1 | 1 | 1 | 1 | 1 |
| Tyloxapol | 0.300 | 0.300 | 0.01 | 0.01 | 0.01 | 0.01 | 0.01 |
| Methocel ® K4M | 0.2 | — | — | 0.01 | — | — | 0.01 |
| Methocel ® F4M | — | — | — | — | 0.01 | — | — |
| Merquat ® 550 | — | 2 | 0.556 | — | — | 0.278 | 0.01 |
| Methylparaben | — | 0.18 | 0.18 | 0.18 | 0.18 | 0.18 | 0.18 |
| EDTA disodium salts | 0.100 | 0.1 | 0.1 | 0.1 | 0.1 | 0.1 | 0.1 |
| Glycerin | 2.50 | 2.50 | 2.50 | 2.50 | 2.50 | 2.50 | 2.50 |
| NaOH pH 5.0-5.5 | QS | QS | QS | QS | QS | QS | QS |
| Purified water | 95.775 | 93.595 | 95.33 | 95.775 | 95.775 | 95.61 | 95.775 |
| Total | 100 | 100 | 100 | 100 | 100 | 100 | 100 |

The molar ratio of water insoluble corticosteroid, polymer (e.g., non-ionic polymer), and surfactant can be between about 1:0.000001:0.001 to about 1:0.01:0.49. Another example of this molar ratio is between about 1:0.0014:0.002 to about 1:0.006:0.15. These ratios are typically used when a non-ionic polymer is present, but can also apply when an ionic polymer is present.

Pharmaceutically acceptable excipients, as used herein, include anything that one of ordinary skill in the art would add to a composition in order to aid in its manufacture, stability, marketing, etc. Examples of excipients include, but are not limited to, preservatives (e.g., EDTA salts), glycerin, mineral oil, additional surfactants (e.g., Brij® 72 and Brij® 721), base (e.g., sodium hydroxide), acid (e.g., hydrochloric acid), methyl paraben, and water.

As an example, the present invention includes oil/lotion based suspensions. This type of suspension includes an oil (e.g., mineral oil) and a second surfactant capable of emulsifying the oil. The second surfactant can be two (or more) surfactants. Surfactants capable of emulsifying oil in pharmaceutical compositions are well known. Examples of sur- The following procedures can be used to manufacture the formulations of the present invention. The non-ionic polymer, METHOCEL® F4M, hydroxypropylmethylcellulose, is used as a non-limiting example.

1. Heat the purified water to 57-85° C., dissolve disodium edentate and tyloxapol first, then dissolve methylparaben. Disperse the METHOCEL® F4M hydroxypropylmethylcellulose and then cool to about 30° C. (METHOCEL® hydroxypropylmethylcellulose does not dissolve in hot water, so first disperse it in hot water and upon cooling, the METHOCEL® hydroxypropylmethylcellulose solution will become clear.)
2. Add glycerin to the vehicle in Step 1 and mix to dissolve.
3. For active drug substances, dissolve the water soluble drug substance (Polymyxin B sulfate in this example) in the vehicle first.
4. Add and disperse the water insoluble clotrimazole and etiprednol dicloacetate. High shear mixer would facilitate the dispersion for better uniformity.
5. Adjust the pH and QS to the final proper weight.

Formulation 1578-90D (METHOCEL® F4M hydroxypropylmethylcellulose 0.01%, tyloxapol 0.01%) can be resuspended easily when compared to formulation 1578-57A, which comprises higher concentration of non-ionic polymer (0.2%) and surfactant (0.3%). It takes about 25~30 vigorous shakes to suspend the drug substances in formulation 1578-57A. It takes only about 4 shakes for formulation 1578-90D. As non-ionic polymer concentration increases, it becomes harder to re-suspend the water insoluble corticosteroid.

The following additional formulations demonstrated the applicability of this type of formulation to other steroids (hydrocortisone acetate, betamethasone dipropionate, betamethasone valerate, triamcinolone acetonide) as well as polymer (KLUCEL hydroxypropylcellulose, NATROSOL hydroxyethylcellulose, METHOCEL® hydroxypropylmethylcellulose, polyethylene glycol, polyvinyl alcohol, xanthan gum) combinations:

after induction of inflammation. In the treatment group, the anti-inflammatory treatment was applied to one ear, one hour after croton oil application; the opposite ear was left untreated. Assessment of the reduction in ear-weight and ear-thickness on the non-treated earlobe was performed 3 hours after treatment application. Since the measurement is performed on the untreated ear, the reduction of ear weight or thickness is due to the drug that reached the untreated ear from systemic circulation after absorption of drug at the area of treatment. Results showed statistical significance ($p<0.05$) when the aqueous formulation with low concentration of surfactant and non-ionic polymer (Formulation 2170-79 & 2170-64) was compared to pure mineral oil formulation or aqueous formulation with no polymer (Formulation 2170-20).

| Ingredients | Steroid-antimicrobial suspensions | | | |
|---|---|---|---|---|
| | 2170-90 % w/w | 2170-93-3 % w/w | 2170-96-TRM10 % w/w | 2170-96-TRM17 % w/w |
| Hydrocortisone Acetate, Microniced | 1.12 | — | — | — |
| Etiprednol dicloacetate Micronized | — | 0.1 | — | — |
| Triamcinolone acetonide Micronized | — | — | 0.1 | 0.1 |
| Clotrimazole Micronized | 1.00 | 1.00 | 1.00 | 1.00 |
| Tyloxapol | 0.010 | 0.01 | 0.01 | 0.01 |
| Hydroxypropyl methylcellulose (Methocel® F4M) | 0.010 | — | 0.01 | — |
| Hydroxypropyl cellulose, Klucel GF | — | 0.01 | — | — |
| Polyethylene glycol, Polyox WSR N60K | — | — | — | 0.01 |
| Methylparaben | 0.18 | 0.18 | 0.18 | 0.18 |
| EDTA disodium Salts | 0.100 | 0.1 | 0.1 | 0.1 |
| Glycerin | 2.50 | 2.50 | 2.50 | 2.50 |
| NaOH pH 5.0-5.5 | QS | QS | QS | QS |
| Purified Water | 95.775 | 95.775 | 95.775 | 95.775 |
| Total | 100 | 100 | 100 | 100 |

| Ingredients | Steroid-antimicrobial suspensions | | | | |
|---|---|---|---|---|---|
| | 2170-96-BD5 % w/w | 2170-96-BD-15 % w/w | 2170-96-BV4 % w/w | 2170-96-BV15 % w/w | 2170-96-BV20 % w/w |
| Betamethasone dipropionate, Micronized | 0.10 | 0.10 | — | — | — |
| Btamethasone valerate, Micronize | — | — | 0.10 | 0.10 | 0.10 |
| Clotrimazole Micronized | 1.00 | 1.00 | 1.00 | 1.00 | 1.00 |
| Tyloxapol | 0.01 | 0.01 | 0.01 | 0.01 | 0.01 |
| Hydroxyethylcellulose, Natrosol 250H | 0.01 | — | — | — | — |
| Hydroxyethylcellulose, Natrosol 250HHX | — | — | 0.01 | — | — |
| Polyvinal alcohol (Celvol V540) | — | 0.01 | — | 0.01 | — |
| Xanthan gum (Kaltrol) | — | — | — | — | 0.01 |
| Methylparaben | 0.18 | 0.18 | 0.18 | 0.18 | 0.18 |
| EDTA disodium Salts | 0.10 | 0.1 | 0.1 | 0.1 | 0.1 |
| Glycerin | 2.50 | 2.50 | 2.50 | 2.50 | 2.50 |
| Purified Water | 95.775 | 95.775 | 95.775 | 95.775 | 95.775 |
| Total | 100 | 100 | 100 | 100 | 100 |

The formulation with low concentration of surfactant (for example Tyloxapol at 0.01%) and non-ionic polymer (for example METHOCEL® F4M hydroxypropylcellulose at 0.01% w/w) also reduced the systemic absorption of anti-inflammatory corticosteroids when applied topically. This was demonstrated in a validated mouse model as follows.

In the following experiment, the irritant, croton oil, was applied to one earlobe of the mice in the untreated control group and to both earlobes of the mice in the treatment groups to induce inflammation. The control group was left untreated Systemic effect of aqueous suspension and oil suspension on the opposite non-treated ear,

| Ear weight (mg) mean +/− sd | | |
|---|---|---|
| N = 20 | N = 20 | N = 20 |
| Untreated control | Betamethasone 0.1% in | Betamethasone 0.1% in |

-continued

| group | aqueous formulation 2170-64* group | pure mineral oil* group |
|---|---|---|
| 47.53 +/− 5.66 | 40.18 +/− 4.29$^a$ | 34.93 +/− 3.09$^{a,b}$ |
| Reduction in systemic effect= | (40.18-47.53)/(34.93-47.53) × 100 = 58% | |

Ear thickness (×10$^{-2}$ mm)) mean +/− sd

| N = 20 | N = 20 | N = 20 |
|---|---|---|
| Untreated control group | Betamethasone 0.1% in aqueous formulation 2170-64* group | Betamethasone 0.1% in pure mineral oil* group |
| 36.4 +/− 4.85 | 28.95 +/− 3.97$^a$ | 24.92 +/− 2.20$^{a,b}$ |
| Reduction in systemic effect= | (28.95-36.4)/(24.92-36.4) × 100 = 65% | |

Systemic effect of two aqueous suspensions on the opposite non-treated ear,

Ear weight (mg) mean +/− sd

| N = 40 | N = 20 | N = 20 |
|---|---|---|
| Untreated control group | Etiprednol dicloacetate 0.2% in aqueous suspension 2170-79* with 0.01% polymer | Etiprednol dicloacetate 0.2% in aqueous suspension 2170-20* with. no polymer |
| 46.51 +/− 4.77 | 39.34 +/− 6.27$^a$ | 35.75 +/− 3.27$^{a,b}$ |
| Reduction in systemic effect | (39.34-46.51)/(35.75-46.51) × 100 = 67% | |

Ear thickness (×10$^{-2}$ mm)) mean +/− sd

| N = 40 | N = 20 | N = 20 |
|---|---|---|
| Untreated control group | Etiprednol dicloacetate 0.2% in aqueous suspension 2170-79* with 0.01% polymer | Etiprednol dicloacetate 0.2% in aqueous suspension 2170-20* with. no polymer |
| 34.58 +/− 4.58 | 28.60 +/− 3.95$^a$ | 25.40 +/− 3.23$^{a,b}$ |
| Reduction in systemic effect | (28.60-34.58)/(25.40-34.58) × 100 = 65% | |

*See below for formulation.
ANOVA (p < 0.05; Two-sides)
$^a$Statistically significant when compared to the untreated control group
$^b$Statistically significant when compared to the formulation 2170-64 or 2170-79

ED-Otic suspension

| Ingredients | 2170-20 series % w/w | 2170-79 series % w/w | 2170-64 with betamethasone % w/w | Betamethasone in mineral oil % w/w |
|---|---|---|---|---|
| Etiprednol dicloacetate | 0.2-0.8 | 0.05-0.2 | — | — |
| Betamethasone | — | — | 0.1 | 0.1 |
| Tyloxapol | 0.300 | 0.01 | 0.01 | — |
| Methocel ® F4M | — | 0.01 | 0.01 | — |
| Methylparaben | 0.18 | 0.18 | 0.18 | — |
| EDTA disodium Salts | 0.050 | 0.1 | 0.1 | — |
| Glycerin | 2.500 | 2.50 | 2.50 | — |
| Mineral oil | — | — | — | QS |
| NaOH pH 5.0-5.5 | QS | QS | QS | — |
| Purified Water | 95.775 | 95.775 | 95.775 | — |
| Total | 100 | 100 | 100 | 100 |

When comparing re-suspensions of (1) an aqueous based suspension and (2) an oil/lotion based suspension, it was found that the better choice was the oil/lotion based suspension. Surprisingly, the suspension in oil/lotion improved upon aging as it stayed suspended for a longer period than the non-lotion suspension (i.e., no mineral oil or BRIJ® surfactants). Oil/lotion based suspension have an oil (e.g., mineral) that is suspended by the presence of a surfactant (e.g., BRIJ® 72 and 721 etherified polyethylene glycols). The surfactant of the oil/lotion based suspension is in addition to the first surfactant discussed previously. An example of an oil/lotion formulation is shown below.

| Oil/lotion based suspension | |
|---|---|
| Ingredient | % w/w |
| Etidprednol dicloacetate, micronized | 0.2 |
| Clotrimazole, micronized | 1 |
| Polymyxin B sulfate USP | 0.1375 |
| Tyloxapol USP | 0.01 |
| disodium Edetate, USP | 0.1 |
| Glycerine USP | 2.5 |
| Hypromellose USP 2906 (Methocel ® F4M) | 0.01 |
| Merquat ® 550 9% | 0.12 |
| Light mineral oil | 2 |
| Brij ® 72 (Polyethylene Glycol 2 Sterayl ether)* | 0.45 |
| Brij ® 721 (Polyethylene Glycol 21 Sterayl ether)* | 0.55 |
| Sodium hydroxide NF | 0.001 |
| Sodium hydroxide NF adjust pH to 5.0~5.5 | QS |
| Hydrochloric acid, adjust pH to 5.0~5.5 | QS |
| Purified water USP, QS | QS |

*Brij ® 72 and Brij ® 721 are surfactants the act in combination as the second surfactants of the present invention.

What is claim is:

1. A method for reducing inflammation of an inflamed area of skin or an ear canal, comprising contacting the inflamed area with an aqueous topical composition in the form of a suspension comprising:
    a) a water insoluble corticosteroid,
    b) at least one ionic polymer selected from the group consisting of xanthan gum and copolymers of diallyl dimethyl ammonium chloride and acrylamide, and
    c) from 0.005 to 0.3% w/w of a surfactant;
    wherein the molar ratio of corticosteroid to polymer to surfactant is 1:0.0014:0.002 to 1:0.006:0.15 and wherein said aqueous topical composition is low in residues, re-suspends easily and exhibits reduced systemic absorption of the water insoluble corticosteroid as compared to a mineral oil suspension of the water insoluble corticosteroid or an analogous aqueous topical composition that does not contain ionic polymer.

2. A method for reducing inflammation of an inflamed area, comprising contacting the inflamed area with an aqueous topical composition in the form of a suspension, comprising:
    a) a water insoluble corticosteroid,
    b) a non-ionic polymer, in an amount of up to 0.05% w/w, and
    c) from 0.005 to 0.2% w/w surfactant,
    wherein the molar ratio of corticosteroid to polymer to surfactant is 1:0.0014:0.002 to 1:0.006:0.15 and wherein said aqueous topical composition is low in residues, re-suspends easily and exhibits reduced systemic absorption of the water insoluble corticosteroid as compared to a mineral oil suspension of the water insoluble corticosteroid or an analogous aqueous topical composition that does not contain non-ionic polymer.

3. The method of claim 1, wherein the corticosteroid is a soft steroid having anti-inflammatory activity.

4. The method of claim 3, wherein the soft steroid is loteprednol etabonate or etiprednol dichloacetate or a mixture thereof.

5. The method of claim 1, wherein the aqueous topical composition is further comprised of a first antimicrobial agent.

6. The method of claim 5, wherein the aqueous topical composition is further comprised of a second antimicrobial agent.

7. The method of claim 1, wherein the surfactant is tyloxapol.

8. The method of claim 7, wherein 0.01% w/w of tyloxapol is present in the aqueous topical composition.

9. The method of claim 1, wherein 0.005 to 2% w/w of the ionic polymer is present in the aqueous topical composition.

10. The method of claim 9, wherein the ionic polymer is a polyquaternium 7.

11. The method of claim 1, wherein the aqueous topical composition further comprises from 0.005 to 0.1% w/w of a non-ionic polymer.

12. The method of claim 11, wherein 0.01% w/w of the non-ionic polymer is present in the aqueous topical composition.

13. The method of claim 11, wherein the non-ionic polymer is hypromellose 2906.

14. The method of claim 1, wherein the aqueous topical composition further comprises one or more pharmaceutically acceptable excipients.

15. A method for reducing inflammation of an inflamed area of skin or an ear canal, comprising contacting the inflamed area with an aqueous topical composition which is an oil/lotion based suspension comprising:
   a) a water insoluble corticosteroid,
   b) an ionic polymer
   c) from 0.005 to 0.3% w/w of a first surfactant, and
   d) an oil suspended by the presence of a second surfactant;
   wherein the molar ratio of corticosteroid to polymer to first surfactant is 1:0.0014:0.002 to 1:0.006:0.15 and wherein said aqueous topical composition re-suspends easily and exhibits reduced systemic absorption of the water insoluble corticosteroid as compared to a mineral oil suspension of the water insoluble corticosteroid or an analogous aqueous topical composition that does not contain ionic polymer.

16. The method of claim 15, wherein the second surfactant is present in the oil/lotion based suspension in a molar ratio of corticosteroid to second surfactant of from 1:1.2 to 1:10.

17. The method of claim 16, wherein the oil is mineral oil, and wherein the second surfactant is a pair of surfactants that are capable of emulsifying mineral oil.

18. The method of claim 17, wherein the second surfactant is a pair of surfactants comprising polyethylene glycol 2 stearyl ether and polyethylene glycol 21 stearyl ether.

19. The method of claim 1, wherein the corticosteroid is selected from the group consisting of etiprednol dicloacetate, loteprednol etabonate and mixtures thereof and 0.2% w/w is present in the aqueous topical composition, the ionic polymer is a polyquaternium 7, and the surfactant is tyloxapol and 0.01% w/w is present in the aqueous topical composition.

20. The method of claim 15, wherein the oil/lotion based suspension is comprised of 1% w/w clotrimazole, 0.01% w/w of hypromellose 2906, 2% w/w mineral oil, 0.45% w/w of polyethylene glycol 2 stearyl ether, and 0.55% w/w of polyethylene glycol 21 stearyl ether.

21. The method of claim 2, wherein the corticosteroid is a soft steroid having anti-inflammatory activity.

22. The method of claim 21, wherein the soft steroid is loteprednol etabonate or etiprednol dichloacetate or a mixture thereof.

23. The method of claim 2, wherein the aqueous topical composition is further comprised of a first antimicrobial agent.

24. The method of claim 23, wherein the aqueous topical composition is further comprised of a second antimicrobial agent.

25. The method of claim 2, wherein the surfactant is tyloxapol.

26. The method of claim 25, wherein 0.01% w/w of tyloxapol is present in the aqueous topical composition.

27. The method of claim 2, wherein at least 0.005% w/w of the non-ionic polymer is present in the aqueous topical composition.

28. The method of claim 27, wherein 0.01% w/w of the non-ionic polymer is present in the aqueous topical composition and the non-ionic polymer is hypromellose 2906.

29. The method of claim 2, wherein the aqueous topical composition is further comprised of from 0.005 to 0.2% w/w of an ionic polymer.

30. The method of claim 29, wherein from 0.01 to 0.2% w/w of the ionic polymer is present in the aqueous topical composition.

31. The method of claim 30, wherein the ionic polymer is a polyquaternium 7.

32. The method of claim 2, wherein the aqueous topical composition is further comprised of one or more pharmaceutically acceptable excipients.

33. A method of reducing inflammation of an inflamed area, comprising contacting the inflamed area with an aqueous topical composition which is an oil/lotion based suspension comprising:
   a) a water insoluble corticosteroid,
   b) a non-ionic polymer in an amount of up to 0.05% w/w,
   c) from 0.005 to 0.3% w/w of a first surfactant, and
   d) an oil suspended by the presence of a second surfactant;
   wherein the molar ratio of corticosteroid to polymer to first surfactant is 1:0.0014:0.002 to 1:0.006:0.15 and wherein said aqueous topical composition re-suspends easily and exhibits reduced systemic absorption of the water insoluble corticosteroid as compared to a mineral oil suspension of the water insoluble corticosteroid or an analogous aqueous topical composition that does not contain non-ionic polymer.

34. The method of claim 33, wherein the second surfactant is present in the oil/lotion based suspension in a molar ratio of corticosteroid to second surfactant of from 1:1.2 to 1:10.

35. The method of claim 34, wherein the oil is mineral oil, and wherein the second surfactant is a pair of surfactants that are capable of emulsifying mineral oil.

36. The method of claim 35, wherein the second surfactant is a pair of surfactants polyethylene glycol 2 stearyl ether and polyethylene glycol 21 stearyl ether.

37. A method for reducing inflammation of an inflamed area of skin or an ear canal, comprising contacting the inflamed area with an aqueous topical composition in the form of a suspension comprising:
   a) a water insoluble corticosteroid,
   b) an ionic polymer, and
   c) from 0.005 to 0.3% w/w of a surfactant;
   wherein the molar ratio of corticosteroid to polymer to surfactant is 1:0.0014:0.002 to 1:0.006:0.15 and wherein said aqueous topical composition is low in residues, re-suspends easily and exhibits reduced systemic absorption of the water insoluble corticosteroid as compared to a mineral oil suspension of the water insoluble corticosteroid or an analogous aqueous topical composition that does not contain ionic polymer.

38. The method of claim 37, wherein the corticosteroid is loteprednol etabonate or etiprednol dichloacetate or a mixture thereof.

39. The method of claim 37, wherein the aqueous topical composition is further comprised of at least one antimicrobial agent selected from the group consisting of polymyxin B sulfate and clotrimazole.

40. The method of claim 37, wherein the surfactant is tyloxapol.

41. The method of claim 37, wherein 0.005% to 0.05% w/w of tyloxapol is present in the aqueous topical composition.

42. The method of claim 37, wherein 0.005 to 2% w/w of the ionic polymer is present in the aqueous topical composition.

43. The method of claim 37, wherein the ionic polymer is selected from the group consisting of xanthan gum, polyquaternium 7 and mixtures thereof.

44. The method of claim 37, wherein the aqueous topical composition is additionally comprised of at least one excipient selected from the group consisting of EDTA salts and glycerin.

45. A method for reducing inflammation of an inflamed area of skin or an ear canal, comprising contacting the inflamed area with an aqueous topical composition which is an oil/lotion based suspension comprising:
   a) a water insoluble corticosteroid,
   b) an ionic polymer
   c) from 0.005 to 0.3% w/w of tyloxapol, and
   d) an oil suspended by the presence of a second surfactant;
   wherein the molar ratio of corticosteroid to polymer to tyloxapol is 1:0.0014:0.002 to 1:0.006:0.15 and wherein said aqueous topical composition re-suspends easily and exhibits reduced systemic absorption of the water insoluble corticosteroid as compared to a mineral oil suspension of the water insoluble corticosteroid or an analogous aqueous topical composition that does not contain ionic polymer.

46. The method of claim 45, wherein the corticosteroid is loteprednol etabonate or etiprednol dichloacetate or a mixture thereof.

47. The method of claim 45, wherein the aqueous topical composition is further comprised of at least one antimicrobial agent selected from the group consisting of polymyxin B sulfate and clotrimazole.

48. The method of claim 45, wherein 0.005 to 0.05% w/w of tyloxapol is present in the aqueous topical composition.

49. The method of claim 45, wherein 0.005 to 2% w/w of the ionic polymer is present in the aqueous topical composition.

50. The method of claim 45, wherein the ionic polymer is a polyquaternium 7, xanthan gum or mixture thereof.

51. The method of claim 45, wherein the second surfactant is present in the oil/lotion based suspension in a molar ratio of corticosteroid to second surfactant of from 1:1.2 to 1:10.

52. The method of claim 45, wherein the oil is mineral oil, and wherein the second surfactant is a pair of surfactants that are capable of emulsifying mineral oil.

53. The method of claim 45, wherein the second surfactant is a pair of surfactants polyethylene glycol 2 stearyl ether and polyethylene glycol 21 stearyl ether.

54. A method for reducing inflammation of an inflamed area of skin or an ear canal, comprising contacting the inflamed area with an aqueous topical composition which is an oil/lotion based suspension comprising:
   a) at least one water insoluble corticosteroid selected from the group consisting of loteprednol etabonate and etiprednol dichloacetate,
   b) xanthan gum
   c) polyquaternium-7,
   d) 0.005 to 0.05% w/w tyloxapol,
   e) mineral oil suspended by the presences of 0.1 to 2% w/w total of polyethylene glycol 2 stearyl ether and polyethylene glycol 21 stearyl ether,
   f) at least one antimicrobial agent
   g) at least one preservative, and
   h) glycerin;
   wherein the molar ratio of corticosteroid to polymer to tyloxapol is 1:0.0014:0.002 to 1:0.006:0.15 and wherein said aqueous topical composition re-suspends easily and exhibits reduced systemic absorption of the water insoluble corticosteroid as compared to a mineral oil suspension of the water insoluble corticosteroid or an analogous aqueous topical composition that does not contain ionic polymer.

* * * * *

UNITED STATES PATENT AND TRADEMARK OFFICE
CERTIFICATE OF CORRECTION

PATENT NO. : 8,653,055 B2  Page 1 of 1
APPLICATION NO. : 11/662538
DATED : February 18, 2014
INVENTOR(S) : Farng et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1433 days.

Signed and Sealed this
Twenty-ninth Day of September, 2015

Michelle K. Lee
*Director of the United States Patent and Trademark Office*